(12) United States Patent
Manoni et al.

(10) Patent No.: US 6,900,311 B2
(45) Date of Patent: May 31, 2005

(54) O-SULPHATED BACTERIAL POLYSACCHARIDES AND THEIR USE

(75) Inventors: Marco Manoni, Milan (IT); Sandro Miletti, Florence (IT); Giovanni Cipolletti, Milan (IT); Rosanna Abbate, Florence (IT); Maria Anna Gori, Pistoia (IT)

(73) Assignee: Inalco S.p.A., Milan (IL)

( * ) Notice: Subject to any disclaimer, the term of this patent is extended or adjusted under 35 U.S.C. 154(b) by 0 days.

(21) Appl. No.: 10/347,992

(22) Filed: Jan. 21, 2003

(65) Prior Publication Data

US 2003/0232785 A1 Dec. 18, 2003

(30) Foreign Application Priority Data

Jun. 12, 2002 (IT) ..................................... MI2002A1294

(51) Int. Cl.[7] ................................................. C07H 1/00
(52) U.S. Cl. ....................... 536/124; 536/18.7; 536/21; 536/123.1
(58) Field of Search ...................... 536/18.7, 21, 123.1, 536/124, 56; 514/54, 56

(56) References Cited

U.S. PATENT DOCUMENTS 6,288,044 B1 * 9/2001 Zoppetti et al. .............. 514/54

OTHER PUBLICATIONS

Leisten et al., "Interleukin–6 Serum Levels Correlate with Footpad Swelling in Adjuvant–Induced Arthritic Lewis Rats Treated with Cyclosporin A or Indomethacin", *Clinical Immunology and Immunopathology*, vol. 56, pp. 108–115 (1990).
Magari et al., "Differential Effects of FK506 and Methotrexate on Inflammatory Cytokine Levels in Rat Adjuvant–Induced Arthritis", *The Journal of Rheumatology*, vol. 30, pp. 2193–2200 (2003).
Lynn et al., "Adjunctive Therapy for Septic Shock: A Review of Experimental Approaches", *Clinical Infectious Diseases*, vol. 20, pp. 143–158 (1995).
SJH Van Deventer (Academic Medical Center Review), "Tumor Necrosis Factor in Crohn's Disease", Gut, vol. 40, pp. 443–448 (1997).
Stack et al., Randomized Controlled Trial of CDP571 Antibody to Tumour Necrosis Factor– in Crohn's Disease, *The Lancet*, vol. 349, pp. 521–524 (1997).

Ikonomidis et al., "Increased Proinflammatory Cytokines in Patients with Chronic Stable Angina and Their Reduction by Aspirin", *Circulation*, pp. 793–798 (1999).
Rodriguez et al., "Structure and Serological Characteristics of the Capsular K4 Antigen of *Escherichia coli* O5: K4:H4, a fructose–containing polysaccharide with a Chondroitin Backbone", *Eur. J. Biochem*.vol. 177, pp. 117–124 (1988).
Manzoni et al., "Production and Purification of An Extracellularly Produced K4 Polysaccharide From *Eschericia coli*", *Biotechnology Letters*, vol. 18, No. 4, p. 383–386 (1966).
Ogamo et al., "Reactivity Toward Chemical Sulfation of Hydroxyl Groups of Heparin", *Carbohydrate Research*, 193 165–172, (1989).
Dengler et al., "Structure of the Serine–Containing Capsular Poly–Saccharide K40 Antigen From *Escherichia coli* O8:K40:H9", *Carbohydrate Research*, 150 233–240, 1986.
Rej et al., "Sulfation of Some Chemically–Modified heparins. Formation of a 3–sulfate analog of heparin", *Carbohydrate Research*, 210, pp. 299–310 (1991).
Tyrrell et al., "Heparin in Inflammation: Potential Therapeutic Applications Beyond Anticoagulation", *Advances in Pharmacology*, vol. 46, pp. 151–208, (1999).
Gaffney et al., "Rheumatoid Arthritis and Heparin", *British Journal of Rheumatology*, vol. 35, No. 8 p. 808, (Mar. 1996).
Salas et al., "Heparin attenuates TNF–α Induced Inflammatory Response through a CD1 1b Dependent Mechanism", *Gut*, vol. 47, pp. 88–96, (2000).
Lever et al., "The effects of heparin and related molecules upon the adhesion of human polymorphonuclear leucocytes to vascular endothelium in vitro", *British Journal of Pharmacology*, 129, pp. 533–540, (2000).
Attanasio et al., "Cytokine Gene Expression in Human LPS– and IFNγ–Stimulated Mononuclear Cells is Inhibited by Heparin", *Thromb Haemost*, vol. 79, pp. 959–962, (1998).
Pepe et al., "Tissue Factor and Plasminogen Activator Inhibitor Type 2 Expression in Human Stimulated Monocytes is Inhibited by Heparin", *Seminars in Thrombosis and Hemostasis*, vol. 23, No. 2, (1997).

* cited by examiner

*Primary Examiner*—Elli Peselev
(74) *Attorney, Agent, or Firm*—Abelman, Frayne & Schwab

(57) ABSTRACT

The present invention refers to the preparation of O-sulphated, N-sulphatated or N-acetylated derivatives, both epimerised or non epimerised, of K5, K4, and optionally defructosilated K4 and K40 polysaccharides and to their use as antiinflammatory agents in chronic and acute inflammations.

8 Claims, 2 Drawing Sheets

O-SULPHATED BACTERIAL POLYSACCHARIDES AND THEIR USE

FIELD OF INVENTION

Object of the present invention is the preparation and use of derivatives of O-sulphated K4 or K5 or K40 *E. coli* polysaccharides as therapeutic products having anti-inflammatory activity.

PRIOR ART

The advantage of the production of active principles from bacteria is the possibility of fermentation on a large scale. In particular, are known to the art processes for the extraction of polysaccharidic precursors of heparin which can be transformed, by means of economically advantageous industrial processes of sulphation, into compounds having heparin-like anti-coagulant activity.

In particular, K4, K5 and K40 polysaccharides consist of repeated sequences of D-glucuronic acid and in one amino-sugar (N-acetylglucosamine for K5 and K40 and N-acetylgalactosamine for K4) and are produced and purified according to known techniques (Manzoni M. Et al. Biotechnology Letters 18(4) 383–386 (1996); Rodriguez M R et al Eur. J. Biochem., 177, 117–124 (1988); Dengler T et al: Carb res. 150, 233–240 (1986)).

The preparation of O-sulphated polysaccharides derivatives has been described by Ogamo A. et al. Carb. Res. 193 (1989) 165–172, and Rej R. N. et al., Carb. Res. 210 (1991) 299–310.

U.S. Pat. No. 5,314,876 relates to the preparation of N and O-sulphated heparosans derived from partially N-deacetylated K5 polysaccharide, which leads to the production of derivatives characterized by a different degree of sulphation and by a degree of acetylation between 0 and 80%.

U.S. Pat. No. 6,288,044 relates to the preparation of O-sulphated K5, K4 and K40 polysaccharides through a process including the direct sulphation of the polysaccharide, in a suspension of an organic solvent, of said polysaccharides in the form of sodium salt. The sulphation leaves intact the acetyl group on nitrogen of the amino-sugar.

This process allows the production of O-sulphated and N-acetylated polysaccharides derivatives in a single reaction; however, the reaction occurs in a heterogeneous phase.

U.S. Pat. No. 6,329,351 B1 refers to the production of sulphated sulphaminoheparosans of K5 polysaccharide through N-deacetylation followed by N-sulphation and O-sulphation. The O-sulphation frees the nitrogen of the glucosamine amino group from the sulphate group thus leaving the amino group free. The obtained product is then N-sulphated in order to obtain O-sulphated and N-sulphated K5 polysaccharides derivatives.

The processes described in patent application WO 01/72848, in WO 97/43317 and in patent U.S. Pat. No. 6,197,943 refer to the preparation of sulphated glycosaminoglycans, derived from K5 polysaccharide, which are differently O-sulphated and epimerized and having a free or sulphated amino group of the glucosamine amino-sugar. Moreover, it is well-known that heparin, some heparin derivatives such as the O-desulphated heparins, the 6O-desulphated heparins and other glycosaminoglycans as for example the dermatan-sulphate and the heparan-sulphate, have biological functions which are distinct from their specific anti-coagulant activity (Tyrrel D J et al. Adv Pharmacology 46, 151–208, 1999; Gaffney and al Br. J. Rheumatology 35, 808, 1996; Salas and al. Gut, 47, 88–96, 2000; Levr et al. Br. J. Pharmacology 129, 533–540, 2000).

Furthermore, it has been demonstrated that heparin restrains the production of IL-1beta, IL-6 and TNF-alpha after induction with LPS (Attanasio M. et al Thromb. Haemost, 79, 959–962, 1998; Pepe G. et al. Thromb. Haemost 23:135–141, 1997).

SUMMARY OF THE INVENTION

The invention refers to the preparation of O-sulphated bacterial polysaccharides derived from KS, K4 and K40 *E.coli* and to their use for the treatment of pathologies due to acute or chronic inflammatory processes and, with particular reference but not limited to, arthritic pathologies (rheumatoid arthritis and osteoarthritis), sepsis, septic shock and intestinal chronic inflammations (ulcerative colitis and Crohn's disease).

K5, K4 or K40 polysaccharides have been O-sulphated in homogeneous phase and N-acetylated. Alternatively, the same polysaccharides have been epimerized, O-sulphated, partially desulphated, N-sulphated or N-acetylated.

These compounds, and in particular O-sulphated, N-acetylated K5 (K5-OSNAc) and O-sulphated, N-sulphated epimerized K5 (K5OSNS epi) obtained according to the present invention show a specific activity on the main cytokines involved in the inflammatory processes inhibiting especially the production of Tumor necrosis factor alpha (TNFalpha), interlukin 1 beta (IL1beta) and interlukin 6 (IL6).

Moreover, the invention concerns the preparation of pharmaceutical mixtures containing these compounds.

DETAILED DESCRIPTION OF THE INVENTION

Figure 1:
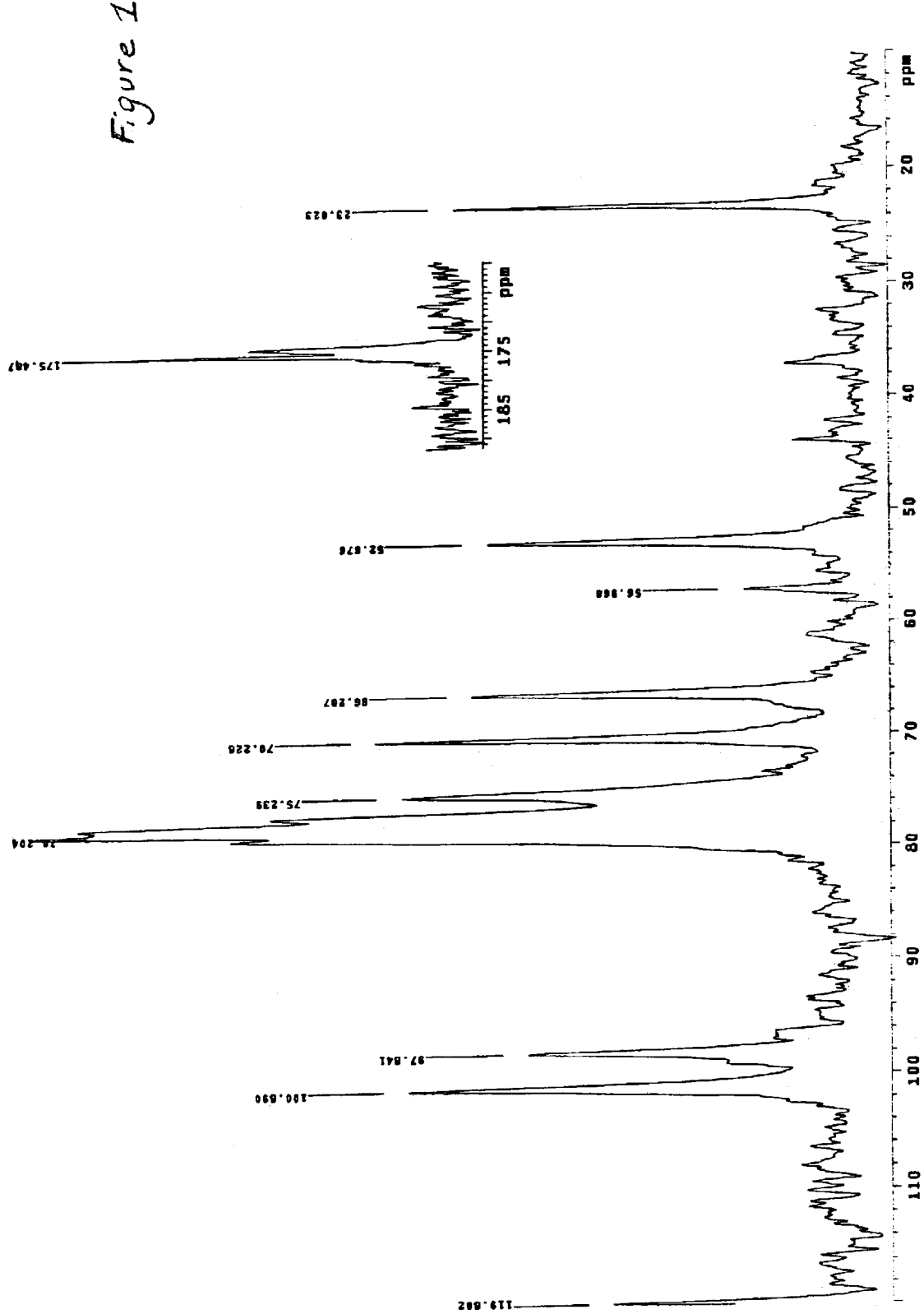
FIG. 1: spectrum $^{13}$C-NMR of the O-sulphated, N-acetylated K5 polysaccharide obtained as described in example 1.
Figure 2:
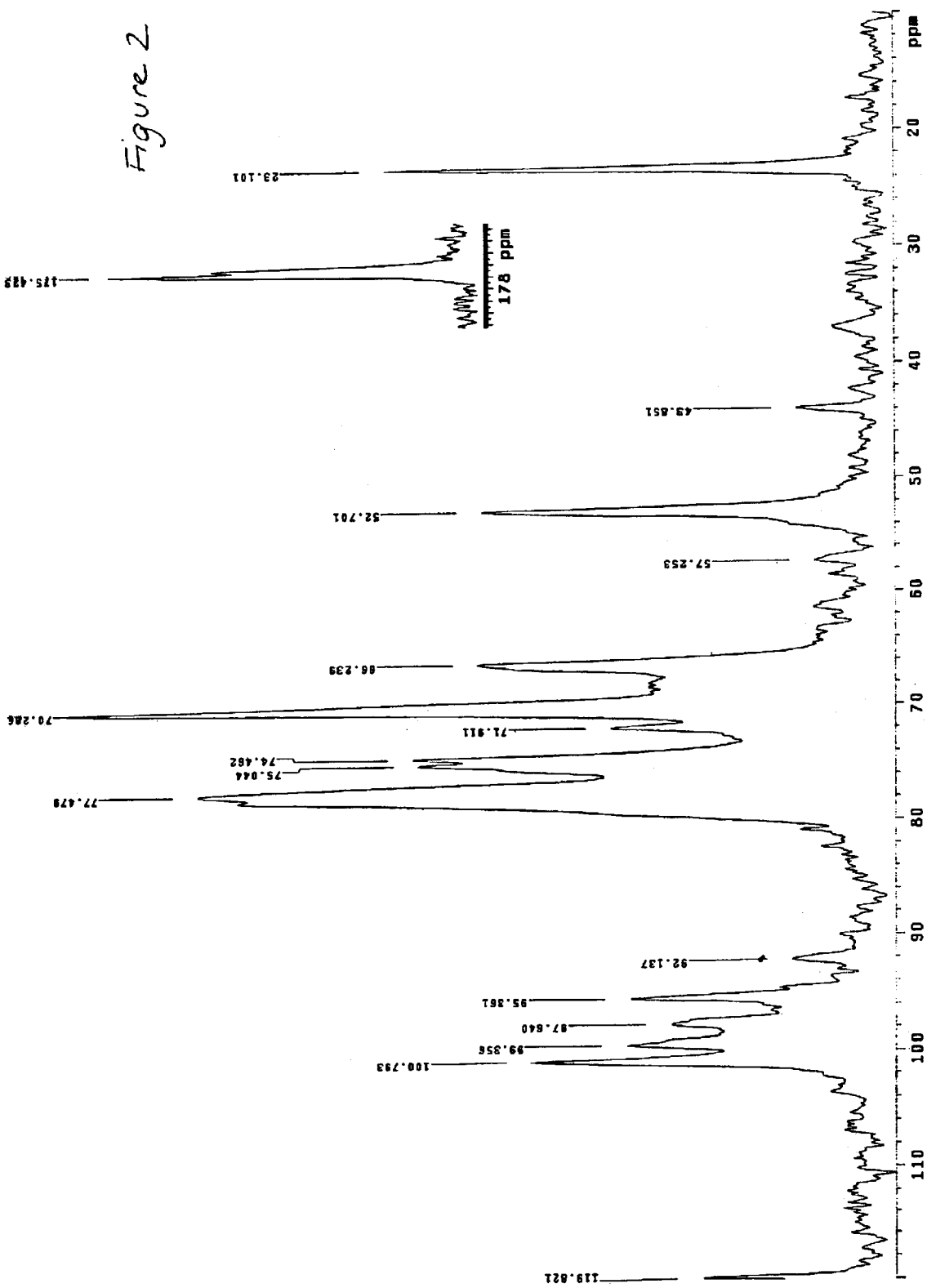
FIG. 2: spectrum $^{13}$C-NMR of the O-sulphated, N-acetylated epimerized K5 polysaccharide obtained as described in example 4.

According to a first embodiment, the invention concerns the use of O-sulphated bacterial polysaccharides derived from K5, K4 and K40 polysaccharides for the preparation of a medicament used for the treatment and prevention of specific pathologies or pathologies associated to an altered production of at least one proinflammatory cytochine.

K5, K4 and K40 polysaccharides, used according to the invention, are produced in *E.coli* and consist of repeated sequences of D-glucuronic acid (substituted if in case) and other amino-sugars (N-acetylglucosamine for K5 and K40 or N-acetylgalactosamine for K4).

In particular the K5 polysaccharide obtained from *E.coli* is a polymer of the disaccharidic unit formed by D-glucuronic acid and N-acetylglucosamine linked by a α 1-[-4)-βGlc-(1,4)-αGlcNAc-(1-] bond. This structure is alike to N-acetylheparosan, the precursory polymer of heparin and of heparan sulphate. This structural affinity with N-acetylated heparin and with desulphated heparin makes the K5 polysaccharide extremely useful to the preparation of sulphated heparin-like semi-synthetic derivatives.

The K4 polysaccharide obtained from *E.coli* is a polymer formed by a sequence of D-glucuronic acid (GlcA) (which is linked to one D-fructose unit in position 3 and N-acetyl galactosamine (GlcNAc) bound by a β1–3 bond. These disaccharidic units are also linked together by a β 1–4 bond.

The K40 polysaccharide obtained from *E.coli* is formed by a trisaccharide consisting in D-glucuronic acid (GlcA) (which is bound to a unit of serine to the carboxyl function) and two units of N-acetyl glucosamine (GlcNAc). The trisaccharidic units (GlcNAc-GlcA-GlcNAc) are linked together by β 1–4 bonds.

The starting K4, K5, K40 polysaccharides are obtained through the fermentation of wild type *E.coli* strains (w.t.) or genetically modified *E.coli* strains. The K4 polysaccharide is generally used after a process of defructosilation carried out, for example, according to the method of Rodriguez et al. Eur. J. Biochem. 1988, 177:177–124. The K40 polysaccharide can be utilised also after elimination of the aminoacid serine.

In the present invention the term re-acetylation means an acetylation process which takes place after deacetylation of the naturally acetylated polysaccharides. Therefore, in the present invention the "N-re-acetylated" products are those which derive from chemical acetylation and not from natural acetylation performed by the microorganism.

Moreover, for the purpose of this invention, partially desulphated polysaccharides are those O-sulphated products obtained through partial desulphation and having a degree of sulphation, defined by the sulphates/carboxyls ratio, below 4 for K4 and K5 polysaccharides and below 6 for K40 polysaccharide.

The O-sulphated products in position 6 are those products presenting a sulphation of the hydroxyl group in position 6 of the amino-sugar.

Under a preferred aspect anti-inflammatory properties are referred in particular to these classes of O-sulphated bacterial polysaccharides:
a) O-sulphated, N-acetylated K5, K4 and K40, obtained through direct sulphation in heterogeneous phase as described in WO 98/34958 and having a natural polysaccharide acetylation;
b) O-sulphated, N-sulphated and epimerized K5 obtained as described in WO 97/43317 and O-sulphated, N-sulphated and epimerized K4;
c) O-sulphated, N-acetylated K5, K4 and K40 characterized by a chemical re-acetylation performed after deacetylation: the resulting polysaccharides are, therefore, defined as re-acetylated. In this case, the sulphation is carried out in homogeneous phase as described for K5 polysaccharide in WO 98/09636; O-sulphated K5 and K4 polysaccharides, optionally epimerized, and N-reacetylated; or the O-sulphated K5 and K4 polysaccharides, epimerized, optionally partially desulphated, and N-reacetylated; or the O-sulphated K5 and K4 polysaccharides, epimerized, partially desulphated, optionally 6 O-sulphated, and N-reacetylated are also endowed with antiinflammatory properties.

Particularly preferred are those reacetylated products derived form K5 polysaccharide, in particular the O-sulphated, N-acetylated K5 (having a degree of acetylation between 80 and 99%) and O-sulphated, N-sulphated and epimerized K5 (having a residual degree of natural acetylation comprised between 0 and 20%).

The anti-inflammatory activity is in particular related to the inhibition of pro-inflammatory cytokines production as observed after the administration of O-sulphated polysaccharides, in an in vitro system represented by human monocytes activated by stimuli such as the bacterial surface antigens (lipopolysaccharide or LPS). During an immune and inflammatory process, the pro-inflammatory cytokines increase many times their level when in the circulation or at the local-level.

In particular, IL-1, IL-6 interlukin and TNF-alpha are considered to be pro-inflammatory cytokines.

The pro-inflammatory cytokines have multiple biological activities and interact with many cellular types. As a matter of fact high levels of these cytokines are found in very different pathologies, such as autoimmune diseases, rheumatoid arthritis, osteo-arthritis, diabetes, intestinal chronic inflammations, sepsis, as described, for example, by Kock A E, et al. 1995; J. Invest. Med. 43:28–38.

Therefore, according to the invention said polysaccharides are useful to the preparation of medicaments for the treatment and prevention of: septic shock, parasitic infections (e.g. malaria), auto immune diseases including some arthritis with particular reference to rheumatoid arthritis, cachexia, cachexia due to bacterial infections such as tuberculosis and meningitis and intestinal chronic inflammatory diseases such as Crohn's disease as well as to those pathologies which are associated to an increase of TNF levels, of IL-1 or IL-6.

Moreover, said polysaccharides are useful to the preparation of medicaments for the treatment and prevention of: inflammatory and immune disorders with particular reference to: psoriasis, Alzheimer's disease, peridontitis connected with an increase of IL-1 beta and IL-6 interlukin, tumour diseases, neurological disorders (e.g. multiple sclerosis, systemic lupus erythematosus, Alzheimer), bacterial and viral meningitis, osteoporosis, due in particular to a disregulation of IL-6 levels.

Cytokines, and in particular IL-1 and TNF, are considered important stimulators of nitrous oxide (NO) production which plays an important role in the immune system functions, in the cardiovascular system and in the bone homeostasis, therefore pathologic diseases which can benefit from the administration of the polysaccharides of the invention, are those by an hyperactivation of Cyclo-oxygenase II (COX-2) induced in many inflammatory processes, wherein their administration may lead to a further reduction of the inflammatory process.

Therefore, among the advantages conferred by the use as anti-inflammatory of the polysaccharides described in the present invention is their capability to act simultaneously against various pro-inflammatory cytokines, and their structural likeness to heparin, a molecule produced by the "self", together with their limited or even absent anti-coagulant activity. In particular, their capability to reduce at the same time the levels of the most important pro-inflammatory cytokines constitutes an advantage compared with many already known anti-inflammatory preparations, as confirmed also by clinical tests carried out with inhibitors specific for a single cytokine.

According to a further embodiment, this invention also refers to O-sulphated and N-acetylated polysaccharides selected from the group of K5, K4, K40 chemically reacetylated for pharmaceutical use. These polysaccharides are optionally further modified through epimerization or through partial desulphation or sulphation in position 6 of the amino-sugar and, in this latter case, they are limited to the polysaccharides derived from K5 and K4.

Particularly preferred polysaccharides are those deriving from the K5 polysaccharide and in particular the O-sulphated, N-reacetylated K5 polysaccharide.

O-sulphated and N-acetylated products derived from sulphation in homogeneous phase and from a chemical reacetilylation process, which represents one of the further embodiment of the invention, in particular K5, K4, defructosilated K4, K40, optionally deserinated, are clearly distinguishable from the relevant naturally acetylated O-sulphated products (i.e. which do not undergo deacetylation and reacetylation) for the following structural peculiarities:

degree of sulphation of position 3 of the N-acetylglucosamine and of position 2 and 3 of glucuronic acid higher than 80%;

degree of acetylation lower than 100%, preferably comprised between 20–99%, or more preferably comprised between 50–95% where 100% is the degree of acetylation of the relevant naturally acetylated polysaccharides;

molecular weight of about 10–40% lower than the molecular weight of the relevant naturally acetylated (i.e. not deacetylated and not reacetylated) O-sulphated polysaccharides;

NMR spectrum different from the spectrum of the relevant naturally acetylated polysaccharides and which correspond, for the N-reacetylated, O-sulphated K5 polysaccharide, to the NMR spectrum shown in FIG. 1.

The O-sulphated and N-reacetylated polysaccharides according to this invention are characterized by a molecular weight from 1,000 to 60,000 Da, preferably ranging from 5,000 to 25,000, by a sulphates/carboxyls ratio (definable also as degree of sulphation) ranging from 0.5 to 4.0, preferably ranging from 3 to 4 and more preferably ranging from 3.5 to 4.0, and by a N-acetylation degree lower than 100%, preferably between 20 and 99%, and more preferably ranging between 50 and 95%. However it has to be taken under consideration that molecular weight of the final compounds can be further reduced, according to known chemical, physic or enzymatic depolymerisation techniques, to products with a lower molecular weight according to the envisaged uses.

According to a further aspect of the present invention, said polysaccharides are useful in particular for the preparation of medicaments for the treatment and prevention of: septic syndrome and septic shock, parasitic infections (e.g. malaria), neoplastic diseases, autoimmune diseases including some arthritis, osteoarthritis and especially rheumatoid arthritis, viral infections (e.g. AIDS), cachexia connected to bacterial infections such as tuberculosis and inflammatory meningitis, in myocardial ischemia, in atherosclerotic diseases and in intestinal chronic inflammatory pathologies such as Chron's disease, associated to an increase of TNF levels.

Moreover, said polysaccharides are useful for the preparation of medicaments for the treatment and prevention of: autoimmune inflammatory disorders such as psoriasis, neurological disorders (e.g. multiple sclerosis, systemic lupus erythematosus), Alzheimer's disease, peridontitis connected with an increase of IL-1 beta and IL-6 interlukin levels, tumour diseases, bacterial and viral meningitis, osteoporosis and rheumatoid arthritis, i.e. diseases associated with an increase of IL-6 levels.

Furthermore since cytokines, and in particular IL-1 and TNF, are considered to be important stimulators of nitrous oxide (NO) which plays an important role in the immune system functions, in the cardiovascular system and in the bone homeostasis, such pathologic conditions can, therefore, benefit from the administration of the polysaccharides described under this invention. The administration of the polysaccharides described in this invention may be useful therefore in those pathologic conditions due to an hyperactivation of the Cyclo-oxygenase II (COX-2) induced in many inflammatory diseases, leading, therefore, to an additional further reduction of the inflammatory process.

The products described in the present invention are used alone or in combination among them or among other active principles, in pharmaceutical preparations for the prevention, relief and treatment of diseases and conditions connected with pathologic variations in the production of pro-inflammatory cytokines such as acute or chronic inflammatory processes. Such therapeutic properties are extended to the derivatives (salts etc.) of the polysaccharides of the invention which are easily obtained according to known technologies.

The present invention also relates to a process for the preparation of O-sulphated and N-acetylated polysaccharides, selected from a group consisting of: K4, K5 and K40 characterized by the subsequent chemical acetylation of the O-sulphated product (re-acetylation). These O-sulphated polysaccharides are preferably selected from a group consisting of: a) O-sulphated, N-acetylated K5, K4 and K40 obtained through direct sulphation in heterogeneous phase preferably essentially as described in WO 98/34958 and where the acetylation is naturally present in the polysaccharide; b) O-sulphated, N-sulphated and epimerized K5 and K4 obtained as described in WO 97/43317; c) O-sulphated, N-acetylated K5, K4 and K40 where the sulphation is carried out in homogeneous phase preferably essentially as described in WO 98/09636, which is therefore incorporated by reference and characterized by chemical reacetylation carried out after deacetylation (these polysaccharides are, therefore, defined as reacetylated); O-sulphated, epimerized, N-re-acetylated K5 and K4; O-sulphated, epimerized, partially desulphated and N-reacetylated K5 and K4; 0-sulphated, epimerized, partially desulphated, 6 O-sulphated and N-reacetylated K5 and K4. In the re-acetylated products the acetylation degree is advantageously chemically modulated to obtain polysaccharides with the most suited physico-chemical properties.

The reacetylated products derived from the K5 polysaccharide are particularly preferred, in particular the O-sulphated, N-reacetylated K5 (with a degree of acetylation lower than 100% preferably comprised between 50% and 95%) and the O-sulphated, N-sulphated and epimerized K5, having a residual degree of natural acetylation comprised between 0 and 20%.

Under yet another preferred embodiment, the process is characterized by the fact that the O-sulphated polysaccharides selected from a group consisting of:

K5 OS($NH_2^+$);
K4 OS($NH_2^+$);
K40 OS($NH_2^+$);
K5 OS($NH_2^+$) epimerized;
K4 OS($NH_2^+$) epimerized;
K5 OS($NH_2^+$) epimerized, partially desulphated and optionally 6O sulphated;
K4 OS($NH_2^+$) epimerized, partially desulphated and optionally 6O sulphated;

are acetylated at pH ranging from 7 to 9 by acetic anhydride treatment at a concentration between 3 and 20%, at temperature between 10° C. and 35° C. and for a time preferably ranging from 1 to 10 hours. Under a preferred method, the acetylation is performed by the addition of a quantity from 0.5 to 4.0 equivalents of NaOH and from 0.5 to 4.0 equivalents of acetic anhydride with respect to the moles of O-sulphated polysaccharide at pH preferably ranging from 7.5 to 8.0 and stirred for a time preferably ranging from 1 to 3 hours, at temperature preferably comprised between 20° C. and 30° C.

K4, K5 and K40 polysaccharides are obtained by fermentation of wild type *E.Coli* strains (w.t.) or of genetically modified *E.Coli* strains. K4 polysaccharide is generally used after defructosilation carried out according, for example, to the method as described by Rodriguez et al. Eur. J. Biochem. 1988,177:117–124. K40 polysaccharide can be used after elimination of the aminoacid serine.

To obtain the reacetylated polysaccharide according to this invention, K4, defructosilated K4, K5, K40 polysaccharides are firstly deacetylated by hydrazine treatment or by highly concentrated hydroxides treatment. Deacetylation is performed preferably through sodium hydroxide or potassium hydroxide with a concentration ranging from 1 to 3 M.

Hydroxides treatment is preferred to hydrazine treatment since it causes a lower depolimerisation of the polysaccharide.

Therefore, according to a particularly preferred embodiment of the preparation process of O-sulphated, N-reacetylated K5, K4, K40 polisaccharides the process comprises essentially the following steps: a) N-deacetylation, b) O-sulphation, c) N-reacetylation.

In step a) the N-deacetylation/N-sulphation of K5, K4 or defructosilated K4 or serine-free K40, is carried out by hydrazine treatment or by highly concentrated hydroxides treatment. Deacetylation is preferably performed with sodium or potassium hydroxide with a concentration ranging from 1 to 3M.

Even more preferably polysaccharides, and in particular purified K5, are solubilized by 100–1000 ml of sodium hydroxide 2 M and then left at a temperature of 40–80° C. up to 30 hours, till deacetylation completion. Thereafter 100–1000 ml of deionized or demineralized water are added to the solution and the mixture is brought to room temperature and to a pH ranging from 7.00 to 9.00 by hydrochloric acid.

To the solution maintained at 20–65° C. and containing the deacetylated polysaccharide is added sodium carbonate and a sulphating agent selected from known sulphating reagents such as sulphur trioxide pyridine adduct or sulphur trioxide trimethylamine. Once the reaction is completed, the solution is taken to room temperature and then to neutral pH preferably between 7–7,5 pH with hydrochloric acid 1M.

The product is purified from salts through known techniques such as diafiltration, then is concentrated under vacuum and precipitated by ethanol or isopropyl alcohol or acetone.

Afterwards, deacetylated polysaccharides are solubilized in $H_2O$ and the solution is cooled down at 4–10° C. Then these polysaccharides are treated through a cation-exchange resin such as the Amberlite IR-120 $H^+$ resin (Rohm & Haas, Paris-France) or equivalent. After the passage of the solution containing the sample, the resin can be washed with deionized water.

The solution containing the sample is then neutralized by addition of a tertiary or quaternary amine such as hydroxide tetrabutylammonium. The solution is reduced to minimum volume and lyophilized.

The obtained tetrabutylammoniurm salt is suspended in 20–1000 ml of N,N-DMF or DMSO and added with 15–300 g of a sulphating agent, for the O-sulphation step b) which is performed by known techniques, and preferably by treatment with $SO_3$-pyridine adduct in solid form or in a solution of N,N-DMF or DMSO. The solution is maintained at a temperature comprised between 20–70° C., preferably between 40–60° C. for a time comprised between 2–24 hours.

Once the reaction is completed the solution is cooled down at room temperature and the polysaccharide is precipitated by ethanol saturated with Na- or K-acetate or isopropyl alcohol or acetone saturated with sodium chloride up to complete precipitation.

The precipitate is, thereafter, separated from the solvent through, for example, filtration, solubilized by a minimum quantity of an aqueous solution comprising 0,2 M NaCl and the solution is taken to neutral pH, preferably comprised between 7 and 9, more preferably between 7,5–8 through a strong base such as sodium hydroxide 2 M and added with acetone till complete precipitation of the polysaccharide.

The obtained precipitate is solubilized by 100–2000 ml of deionized water, purified from residual salts by ultrafiltration as described in step a) and, finally, dried under vacuum. The product is then reacetylated according to step c) of N-acetylation. The obtained polysaccharide is then solubilized in deionized $H_2O$ at room temperature; to the solution are, therefore, added between 0.5 and 4 equivalents of NaOH and between 0.5 and 4 equivalents of acetic anhydride with respect to the moles of O-sulphated polysaccharide. The solution is taken to neutral pH, preferably between 7 and 9, more preferably if between 7,5–8 with sodium hydroxide 2M and stirred for 1–3 hours at room temperature.

Afterwards the product is purified from salts through known techniques such as diafiltration using a spiral wrapped membrane with a size exclusion of about 1,000 D. The process is completed once the conductivity of the permeate is lower than 100 $\mu S$. The obtained product is concentrated under vacuum up to dryness at a temperature of 30–60° C.

According to a further aspect, the process according to the present invention concerns the preparation of epimerized O-sulphated, N-acetylated derivatives comprises essentially the following steps:

a) N-deacetylation/N-sulphation of the K5 or K4 polysaccharides.
b) Epimerization
c) O-sulphation
d) N-acetylation (re-acetylation).

Step a) concerning N-deacetylation/N-sulphation of K5 or K4 or defructosilated K4 polysaccharides is carried out by hydrazine treatment or by highly concentrated hydroxides treatment. Deacetylation is performed preferably by sodium or potassium hydroxide in concentration ranging from 1 to 3 M. Hydroxides treatment is preferred to hydrazine treatment since it causes a lower de-polymerisation in the polysaccharide.

More preferably the polysaccharides, with particular reference to the purified K5, are solubilized by 100–1000 ml of sodium hydroxide 2 M and kept at 40–80° C. for a time up to 30 hours till complete deacetylation. Thereafter 100–1000 ml of deionized or demineralized water are added to the solution which is brought to room temperature and then to pH ranging from 7.00 to 9.00 by hydrochloric acid.

The solution containing the deacetylated polysaccharide is maintained at 20–65° C. and then added with sodium carbonate and a sulphating agent selected from known sulphating reagents such as sulphur trioxide pyridine adduct or sulphur trioxide trimethylamine. Once the reaction is completed, the solution is taken to room temperature and to neutral pH, preferably at pH between 7 and 9, more preferably between 7 and 7.5, for example by hydrochloric acid 1M.

The product is purified from salts through known techniques such as diafiltration, then is concentrated under vacuum and precipitated by ethanol or isopropyl alcohol or acetone.

In step b) the epimerization is carried out in position C5 of the glucuronic acid of K5 polysaccharide (and defructosilated K4) then, in compliance with this aspect of the present invention, it is performed by the glucuronyl C5 epimerase enzyme in solution or in immobilized form.

The enzymatic epimerization is carried out through known techniques such as those described in patent WO 01/72848 where C5 epimerase enzyme, natural or recombinant, is immobilized on inert support which can be a resin functionalized with reactive groups using common techniques of activation and binding for enzymes such as CNBr. Particularly preferred is the epimerization carried out by dissolving in 20–1000 ml of solution 25 mM Hepes, 0.1 M KCl, 0.01% tritonX100, 0.15 M EDTA at pH 6–7.4, an amount between 0.001 and 10 g of N-deacetylated N-sulphated K5 polysaccharide, which is recirculated at 30–160 ml/hr for 1–48 hrs in a thermostatic column at 30–40° C., containing $1.2 \times 10^7$ to $3 \times 10^{11}$ cpm eq. of immobilized enzyme. Once the reaction is completed the sample is purified through passage on DEAE resin or by precipitation with 2 volumes of ethanol. As for K4 polysaccharide (defructosilated), the epimerization is carried out with glucuronil C5 epimerase enzyme in compliance with the conditions described by Hannesson HH et al. Biochem J. 15, 313; 589–596,1996.

Thereafter, the deacetylated polysaccharides are solubilized in $H_2O$ and the solution is then cooled down to 4–10° C. and, afterwards, said polysaccharides are treated through a cation-exchange resin such as Amberlite IR-120 $H^+$ (Rohm & Haas, Paris-France) or equivalent. After the passage of the solution containing the sample, the resin can be washed with deionized water.

The solution is taken at pH comprised between 6 and 9, preferably between 6,5 and 7,5 with tetrabutylammonium hydroxide and the resulting solution concentrated under vacuum in a small volume and lyophilized.

Step c) concerning the O-sulphation is performed according to known techniques, preferably through treatment by $SO_3$ pyridine adduct in solid form or in a solution of N,N-DMF or DMSO. The solution is maintained at 20–70° C., preferably between 40–60° C. for 2–24 hours.

Once the reaction is completed the solution is cooled down to room temperature and the polysaccharide can be precipitated by ethanol saturated with sodium or potassium acetate or with isopropyl alcohol or acetone saturated with sodium chloride up to complete precipitation.

The precipitate is separated from the solvent, for example by filtration, then solubilized with minimum quantity of 0.2M NaCl and then the solution is taken to neutral pH, preferably comprised between 7 and 9, preferably comprised between 7,5–8 with a strong base as for example sodium hydroxide 2 M and added with acetone till complete precipitation.

The obtained precipitate is solubilized by 100–2000 ml of deionized water, purified from residual salts by ultra filtration as described in step a) and dried under vacuum.

In step d) concerning the N-acetylation, the product is reacetylated: the precipitated polysaccharide obtained according to the foregoing step is solubilized in deionized $H_2O$ at room temperature.

The solution is added with 0.5–2 equivalents of NaOH and with 0.5–2 equivalents of acetic anhydride with respect to the moles of O-sulphated polysaccharide. The solution is taken to neutral pH, preferably between 7 and 9, better if between 7,5–8 with sodium hydroxide 2 M and stirred for 1–3 hours at room temperature.

The product is then purified from salts through known techniques such as diafiltration using a spiral wrapped membrane by 1,000 D. The purification is sufficient when the conductivity of the permeate is lower than 100 S. The obtained product is concentrated under vacuum up to dryness at a temperature ranging from 30 to 60° C.

Under another point of view the invention relates to a process for the preparation of epimerized and partially desulphated and N-acetylated O-sulphated derivatives characterized by the following steps:
   a) N-deacetylation/N-sulphation of polysaccharides, preferably K5 polysaccharide,
   b) Epimerization,
   c) O-sulphation,
   d) Partial desulphation,
   e) N-reacetylation.

In step a) concerning N-deacetylation/N-sulphation of the polysaccharide, preferably K5, the deacetylation is carried out by hydrazine treatment or by highly concentrated hydroxides treatment. Deacetylation is preferably performed by sodium or potassium hydroxide with a concentration ranging from 1 to 3 M.

More preferably the polysaccharides, in particular purified K5, are solubilized by 100–1000 ml of sodium hydroxide 2M and maintained at 40–80° C. up to 30 hours till deacetylation completion. Thereafter 100–1000 ml of deionized or demineralized water are added and the solution is taken to room temperature and then to pH ranging from 7.00 to 9.00 through hydrochloric acid.

The solution containing the deacetylated polysaccharide is maintained at 20–65° C. and added with sodium carbonate and a sulphating agent selected from known sulphating reagents such as sulphur trioxide pyridine adduct or sulphur trioxide trimethylamine. Once the reaction is completed, the solution is brought to room temperature and to neutral pH, preferably at pH comprised between 6.5 and 9, more preferably between 7–7.5, for example by hydrochloric acid 1M.

The product is purified from salts through known techniques such as diafiltration, concentrated under vacuum and precipitated by ethanol or isopropyl alcohol or acetone.

Step b) concerning epimerization brings to epimerization in position C5 of the glucuronic acid of the K5 and defructosilated K4 polysaccharides. The epimerization is performed by the glucuronil C5 epimerase enzyme in solution or in immobilized form. The enzymatic epimerization can be carried out by known techniques such as those in patent WO 01/72848 where C5 epimerase enzyme, natural or recombinant, is preferably immobilized on inert support which can be a resin functionalized with reactive groups using common techniques of activation and binding for enzymes such as CNBr. Particularly preferred is the epimerization carried out by dissolving in 20–1000 ml of solution 25 mM Hepes, 0.1 M KCl, 0.01% tritonX100, 0.15 M EDTA at pH 6–7.4, an amount between 0.001 and 10 g of N-deacetylated N-sulphated K5 polysaccharide, which is recirculated at 30–160 ml/hr for 1–48 hrs in a thermostatic column at 30–40° C., containing $1.2 \times 10^7$ to $3 \times 10^{11}$ cpm eq. of immobilized enzyme. Once the reaction is completed the sample is purified by passing on DEAE resin or by precipitation with 2 volumes of ethanol. As for K4 polysaccharide (defructosilated), the epimerization is carried out with glucuronil C5 epimerase enzyme in compliance with the conditions described by Hannesson H H et al. Biochem J. 15, 313; 589–596, 1996.

Thereafter, the deacetylated polysaccharide is solubilized in $H_2O$ and the solution is cooled down to 4–10° C. and then treated on a cation-exchange resin such as the Amberlite IR-120 $H^+$ (Rohm & Haas, Paris-France) or equivalent. After the passage of the solution containing the sample, the resin can be washed with deionized water.

The solution with optional washing is brought to pH comprised between 6 to 9, preferably from 6,5 to 7,5 with tetrabutylammonium hydroxide. The resulting solution is concentrated under vacuum in a small volume and lyophilized.

Step c) concerning O-sulphation is performed according known techniques, preferably through treatment with $SO_3$ pyridine adduct in solid form or in a solution of N,N-DMF or DMSO. The solution is maintained at 20–70° C., preferably between 40–60° C., for 2–24 hours.

Once the reaction is completed the solution is cooled down to room temperature and the polysaccharide can be precipitated by acetone saturated with sodium chloride up to complete precipitation.

The precipitate is separated from solvent, for example through filtration, solubilized with minimum quantity of an aqueous solution of NaCl 0.2 M and then the resulting solution is taken to neutral pH, preferably between 7 and 9, more preferably between 7.5 and 8 with a strong base such as sodium hydroxide 2 M and added with acetone till complete precipitation.

The obtained precipitate is solubilized by 100–2000 ml of deionized water, purified from residual salts by ultrafiltration as described in step a) and dried under vacuum.

In step d) concerning partial desulphation, the product is solubilized in deionized water and the solution is passed through cation-exchange resin IR-120 $H^+$ or equivalent. The acid solution eluted by $H_2O$ is brought to pH comprised between 6.5–7.5 by adding pyridine and lyophilized.

Preferably the pyridine salt of the polysaccharide is added with 20–2000 ml of a solution of DMSO/methanol according to a 9/1 V/V ratio. The solution is maintained at 45–90° C. for 1–8 hours. Once the reaction is completed, the solution is added with deionized water and the product precipitated by acetone saturated with sodium chloride. The obtained solid is solubilized with deionized water, the pH is brought to pH 7–7.5 and purified through diafiltration on a spiral wrapped membrane having a cut-off of 1000 D and then concentrated and lyophilized under vacuum.

Step e) concerning N-acetylation is carried out through solubilization of the polysaccharide, obtained in step d), in deionized $H_2O$ at room temperature. A quantity ranging from 0.5 to 2 eq. of NaOH and from 0.5 to 2 eq. of acetic anhydride with respect to the moles of O-sulphated polysaccharide are added to the solution. The solution is taken to 7.5–8 pH through sodium hydroxide 2M and stirred for 1–3 hours at room temperature.

The product is then purified from salts through known techniques such as diafiltration using a spiral membrane wrapped by 1,000 D. The purification is completed once the conductivity of the permeate is lower than 100 $\mu$S. The final product is dried under vacuum at a temperature of 30–60° C.

Likewise, the present invention relates to a process for the preparation of epimerized N-acetylated and 6O-sulphated derivatives characterized by the following steps:
a) N-deacetylation/N-sulphation of the polysaccharide,
b) Epimerization
c) O-sulphation
d) Partial desulphation
e) 6O-sulphation
f) N-acetylation.

In step a) concerning N-deacetylation/N-sulphation of the polysaccharide, preferably K5, the deacetylation is carried out by hydrazine treatment or by highly concentrated hydroxides treatment.

Preferably, the deacetylation is performed through sodium or potassium hydroxide in a concentration between 1 and 3 M.

More preferably polysaccharides, particularly purified K5, are solubilized by 100–1000 ml sodium hydroxide 2M and maintained at 40–80° C. up to 30 hours, till complete deacetylation.

A quantity of 100–1000 ml of deionized or demineralized water are added to the solution which is taken to room temperature and to pH ranging from 7.00 to 9.00 with hydrochloric acid.

The solution containing the deacetylated polysaccharide is maintained at 20–65° C. and then added with sodium carbonate and a sulphating agent selected from known sulphating reagents, as for example pyridine-$SO_3$ or trimethylamine-$SO_3$ adducts.

Once the reaction is completed the solution is cooled down to room temperature and taken to neutral pH, preferably between 7 and 7,5 with hydrochloric acid 1M.

The product is purified from salts through known techniques as for example diafiltration, concentrated under vacuum and precipitated by ethanol or isopropyl alcohol or acetone.

In step b) concerning epimerization, the epimerization is carried out in position C5 of the glucuronic acid of K5 and defructosilated K4 polysaccharides.

The epimerization is carried out by C5 epimerase glucuronyl enzyme in solution or in immobilized form.

The enzymatic epimerization is carried out through known techniques such as those described in patent WO 01/72848 where C5 epimerase enzyme, natural or recombinant, is preferably immobilized on inert support which can be a resin functionalized with reactive groups using common techniques of activation and binding for enzymes such as CNBr. Particularly preferred is the epimerization carried out by dissolving in 20–1000 ml of solution 25 mM Hepes, 0.1 M KCl, 0.01% tritonX100, 0.15 M EDTA at pH 6–7.4, an amount between 0.001 and 10 g of N-deacetylated N-sulphated K5 polysaccharide, which is recirculated at 30–160 ml/hr for 1–48 hrs in a thermostatic column at 30–40° C., containing $1.2 \times 10^7$ to $3 \times 10^{11}$ cpm eq. of immobilized enzyme. Once the reaction is completed the sample is purified through passage on DEAE resin or by precipitation with 2 volumes of ethanol. As for K4 polysaccharide (defructosilated), the epimerization is carried out with glucuronyl C5 epimerase enzyme in compliance with the conditions described by Hannesson HH et al. Biochem J. 15, 313; 589–596, 1996.

Afterwards deacetylated polysaccharides are solubilized in H2O and the solution is cooled down to 4–10° C. and then treated through cation-exchange resin IR-120 $H^+$ or equivalent. After the passage of the solution containing the sample, the resin can be washed with deionized water.

The solution is brought to pH comprised from 6 to 9, preferably comprised from 6.5 to 7.5 with tetrabutylammonium hydroxyde. The resulting solution is concentrated under vacuum in a small volume and lyophilized.

Step c) concerning the O-sulphatation is performed through known techniques, preferably through treatment by $SO_3$ pyridine adduct in solid form or in a solution of N,N-DMF or DMSO. The solution is maintained at 20–70° C., preferably between 40–60° C. for 2–24 hours.

Once the reaction is completed the solution is cooled down to room temperature and the polysaccharide is precipitated by ethanol or isopropyl alcohol saturated with sodium or Potassium Acetate or acetone saturated with sodium chloride up to complete precipitation.

The precipitate is separated from the solvent, for example through filtration, then solubilized with minimum quantity of 0.2M NaCl aqueous solution and the solution is taken to neutral pH, preferably comprised between 7.5 and 8 with a strong base, as for example sodium hydroxide 2 M and added with acetone till complete precipitation.

The obtained precipitate is solubilized by 100–2000 ml of deionized water, purified from residual salts by ultrafiltration as described in step a) and then dried under vacuum.

In step d) concerning partial desulphation, the solution containing the obtained product is solubilized with deionized water and passed through cation-exchange IR-120 H$^+$ resin or equivalent. The acid solution, eluted by H$_2$O is then brought to pH comprised between 6.5–7.5 by adding pyridine and lyophilized. The pyridine salt of the polysaccharide is added with 20–2000 ml of a solution of DMSO/methanol according to a 9/1 V/V ratio. The solution is maintained at 45–90° C. for 1–8 hours. Once the reaction is completed, the solution is added with deionized water and precipitated by addition of acetone saturated with sodium chloride. The obtained solid is solubilized with deionized water, the pH is brought to 7–7.5 and the polysaccharide purified through diafiltration on a spiral wrapped membrane having a cut-off of 1000 D and then concentrated and lyophilized under vacuum.

Step e) concerning 6O-sulphation is preceded by salification of the product obtained in d) with hydroxide tetrabutylammonium. The solid is solubilized in deionized water and the solution is treated through a cation exchange resin IR-120M$^+$ or equivalent. After the passage of the solution containing the sample, the resin can be washed with deionized water. The solution is brought to pH comprised from 6 to 9, preferably comprised from 6.5 to 7.5 with tetrabutyl ammonium hydroxide. The resulting solution is concentrated under vacuum in a small volume and lyophilized. The tetrabutylammonium salt thus obtained is suspended in 20–500 ml of DMF. The suspension is then cooled down to 0° C. and it is added with a sulphating agent such as for example, pyridine SO$_3$ adduct.

The solution is maintained at 0–5° C. for a time comprised between 0.5–3 hours.

Then it is added with acetone saturated with sodium chloride up to complete precipitation.

The obtained precipitate is solubilized through 100–2000 ml of deionized water, purified from residual salts by ultrafiltration and dried under vacuum.

The product is then reacetylated, according to step f) concerning N-acetylation. In this step, the polysaccharide resulting from the previous step is solubilized in deionized H$_2$O at room temperature. The solution is added with 0.5–2 equivalents of NaOH and with 0.5–2 equivalents of acetic anhydride with respect to the moles of O-sulphated polysaccharide. The solution is taken to neutral pH, preferably comprised between 7–8 with sodium hydroxide 2M and stirred for 1–3 hours at room temperature.

The product is then purified from salts through known techniques as for example through diafiltration using a spiral wrapped membrane by 1000 D cut-off.

The process is completed when the conductivity of the permeate is lower than 100 µS. The obtained product is concentrated and dried under vacuum at a temperature of 30–60° C.

The present invention relates also to a process for the preparation of products deriving from chemical reacetylation and in particular O-sulphated and N-reacetylated polysaccharides obtainable from N-reacetylation of deacetylated and N-sulphated polysaccharides, with acetic anhydride in a concentration ranging from 3 to 20%, at pH between 7–9, at temperature between 10 and 35° C., of those intermediate products selected from the group consisting of:

K5 OS(NH$_2^+$)
K4 OS(NH$_2^+$)
K40 OS(NH$_2^+$)
K5 OS(NH$_2^+$) epimerized
K4 OS(NH$_2^+$) epimerized
K5 OS(NH$_2^+$) epimerized, partially desulphated, optionally 6O-sulphated
K4 OS(NH$_2^+$) epimerized, partially desulphated, optionally 6O-sulphated The acetylation is preferably carried out after solubilization of the polysaccharide in deionized H$_2$O at room temperature. The solution is added with 0.5–4 eq. of NaOH and with 0.5–4 eq. of acetic anhydride with respect to the moles of O-sulphated polysaccharide. The solution is taken to neutral pH, preferably between 7–9, more preferably between 7.5–8 with sodium hydroxide 2M and stirred for 1–3 hours at room temperature.

The products obtainable by a reacetylation step are recognizable from the corresponding naturally acetylated polysaccharides, as the degree of acetylation can be modulated and standardised and can be maintained lower than 100%, preferably between 20% and 99%, or more preferably between 50% and 95%, wherein a 100% is referred to the degree of acetylation of the naturally acetylated product.

Particularly preferred are those reacetylated products obtained from K5 polysaccharide, in particular O-sulphated, N-reacetylated K5, having a degree of acetylation preferably ranging from 50 to 95%.

Moreover, polysaccharides obtainable through said process are characterized by a characteristic NMR spectrum which, for O-sulphated and N-reacetylated polysaccharides, is different from the spectrum characterizing naturally acetylated polysaccharides. Characteristic is also their molecular weight, which is 10–40% lower than the molecular weight of the corresponding O-sulphated, naturally acetylated products (i.e. not deacetylated and not reacetylated).

According to a further embodiment, the invention relates also to pharmaceutical products containing, as the pharmacologically active ingredient, at least one of the bacterial polysaccharides chosen among: O-sulphated K5, K4, defructosilated K4 and K40 (sulphated through direct sulphation in heterogeneous phase) or at least one of the bacterial polysaccharides chosen among O-sulphated, N-sulphated and epimerized K5, K4, defructosilated K4 for the treatment and prevention of: sepsis, septic shock, osteoarthritis, rheumatoid arthritis, pathologies associated with or characterized by acute inflammation and/or chronic inflammation, ulcerative colitis, Crohn's disease.

Moreover the invention comprises pharmaceutical compositions containing as pharmaceutically active ingredient at least one of the polysaccharides K5, K4, defructosilated K4, K40, O-sulphated (through sulphation in homogeneous phase) and N-reacetylated, optionally even epimerized, and furthermore optionally even partially desulphated and even 6O-sulphated in combination or mixture with a pharmaceutically suitable inert excipient.

The characteristics and the advantages of the products obtained according to this invention and of the process to prepare bacterial polysaccharides used in this invention will be described in details in the experimental section, which does not represent any practical limit.

According to a further embodiment the invention is related to a therapeutic method comprising administering a therapeutically effective amount of an O-sulphated polysaccharide selected in the group consisting of: K5, K4, defructosilated K4, K40 for treating or preventing pathologies resulting from or associated to an altered production of at least a pro-inflammatory cytokine to a patient in need of such a treatment. As a way of example: sepsis, septic shock, osteoarthritis, rheumatoid arthritis or in general autoimmune diseases, pathologies associated with or characterized by acute and/or chronic inflammation, ulcerative colitis, Crohn's disease may benefit from the use of these polysaccharides.

Similarly, is comprised in the present invention a therapeutic method comprising administering a therapeutically effective amount of a O-sulphated and N-reacetylated polysaccharides obtainable by applying the process described and characterized by an acetylation degree lower than the corresponding natural polysaccharide, for treating or preventing pathologies resulting from or associated to an altered production of at least a pro-inflammatory cytokine to a patient in need of such a treatment. As a way of example: sepsis, septic shock, osteoarthritis, neoplastic diseases, rheumatoid arthritis or in general autoimmune diseases, pathologies associated with or characterized by acute and/or chronic inflammation, ulcerative colitis, Crohn's disease, may benefit from the use of these polysaccharides.

EXAMPLE 1

Preparation of O-sulphated, N-acetylated K5 Polysaccharide

Firstly the process was carried out through a) N-deacetylation/N-sulphation: 25 g. of purified K5 polysaccharide are solubilized with 100–1000 ml of sodium hydroxide 2M and maintained at 40–80° C. up to 30 hours, till complete deacetylation.

After the adding of 100–1000 ml of deionized or demineralized water, the solution was taken to 20–30° C. and to pH 7.5 by hydrochloric acid.

The solution containing deacetylated K5 was maintained at 20–65° C. and added with 10–50 g of sodium carbonate and 10–50 g of a sulphating agent selected from sulphating reagents as for example the pyridine sulphur trioxide or trimethylamine sulphur trioxide adduct. The adding of sulphating agent was performed in a time up to 6 hours. After completion of the reaction, the solution was taken to a temperature ranging from 20 to 30° C. and to pH of 7–7.5 by hydrochloric acid 1M.

The product was purified from salts through known techniques, as for example through diafiltration by using a spiral wrapped membrane by 1000 D.

The process was completed when the conductivity of the permeate was lower than 100 $\mu$S. The obtained product was concentrated under vacuum, cooled down to 4–10° C. and precipitated by ethanol or isopropyl alcohol or acetone.
b) O-sulphation: N-deacetylated and N-sulphated K5 polysaccharide was solubilized in $H_2O$ and the solution was cooled down to 4–10° C. and then treated on cation-exchange IR-120H+ resin or equivalent.

After the passage of the solution containing the sample, the resin was washed with deionized water.

The solution containing the sample was then neutralized with tertiary or quaternary amine, as for example tetrabutylamonium hydroxide.

The solution was reduced to minimum volume and lyophilized.

The tetrabutylamonium salt was suspended in 20–1000 ml of N,N-DMF or DMSO and added with 15–300 g of a sulphating agent as for example pyridine $SO_3$ adduct in solid form or in solution of N,N-DMF or DMSO. The solution was maintained at 20–70° C., preferably between 40–60° C. for 2–24 hours.

Once the reaction was completed, the solution was cooled down to room temperature and added with acetone saturated with sodium chloride up to complete precipitation.

The precipitate was separated from the solvent by filtration, solubilized with a minimum quantity of a 0.2 M NaCl aqueous solution and the solution was taken to pH 7.5–8 with sodium hydroxide 2 M and added with acetone up to complete precipitation.

The obtained precipitate was solubilized with 100–2000 ml of deionized water, purified from residual salts by ultrafiltration as described in step a) and dried under vacuum.
c) N-acetylation O-sulphated K5 polysaccharide deriving from step b) was solubilized in deionized $H_2O$ at room temperature. The solution was added with 0.5 to 2 eq. of NaOH and 0.5 to 2 eq. of acetic anhydride with respect to the moles of O-sulphated K5.

The solution was taken to pH 7.5–8 by sodium hydroxide 2 M and stirred at room temperature for 1–3 hours.

The product was then purified from salts through known techniques as for example through diafiltration using a spiral wrapped membrane by 1000 D.

The process was completed when the conductivity of the permeate was lower than 100 $\mu$S. The obtained product was concentrated till dried under vacuum, at a temperature of 30–60° C.

EXAMPLE 2

Preparation of O-sulphated, N-acetylated K4 Polysaccharide

Firstly the process was carried out through a) N-deacetylation/N-sulphation: 25 g. of defructosilated purified K4 polysaccharide are solubilized with 100–1000 ml of sodium hydroxide 2M and maintained at 40–80° C. up to 30 hours, till complete deacetylation.

After the adding of 100–1000 ml of deionized or demineralized water, the solution was taken to a temperature ranging from 20 to 30° C. and to pH 8.00–9.00 by hydrochloric acid.

The solution containing deacetylated K4 was maintained at 20–65° C. and added with 10–50 g of sodium carbonate and 10–50 g of a sulphating agent selected from sulphating reagents as for example the pyridine sulphur trioxide or trimethylamine sulphur trioxide adduct. The adding of sulphating agent was performed in a time up to 6 hours. After completion of the reaction, the solution was taken to a temperature ranging from 20 to 30° C. and to pH 7–7.5 by hydrochloric acid 1M.

The product was purified from salts through known techniques, as for example through diafiltration by using a spiral wrapped membrane by 1000 D.

The process was completed when the conductivity of the permeate was lower than 100 $\mu$S. The obtained product was concentrated under vacuum, cooled down to 4–10° C. and precipitated by ethanol or isopropyl alcohol or acetone.
b) O-sulphation:

The N-deacetylated K4 polysaccharide N-sulphated was solubilized in $H_2O$ and the solution was cooled down to 4–10° C. and then treated on cation-exchange IR-120H+ resin or equivalent.

After the passage of the solution containing the sample, the resin was washed with deionized water.

The solution containing the sample was then neutralized with tertiary or quaternary amine, as for example tetrabutylamonium hydroxide.

The solution was reduced to minimum volume and lyophilized.

The tetrabutylamonium salt was suspended in 20–800 ml of N,N-DMF or DMSO and added with 15–300 g of a sulphating agent as for example pyridine $SO_3$ adduct in solid form or in solution of N,N-DMF or DMSO. The solution was maintained at 20–70° C., preferably between 40–60° C. for 2–24 hours.

Once the reaction was completed, the solution was cooled down to room temperature and added with acetone saturated with sodium chloride up to complete precipitation.

The precipitate was separated from the solvent by filtration, solubilized with minimum quantity of a 0.2 M NaCl solution and the solution was taken to pH 7.5–8 with sodium hydroxide 2 M and added with acetone up to complete precipitation.

The obtained precipitate was solubilized with 100–2000 ml of deionized water, purified from residual salts by ultrafiltration as described in step a) and dried under vacuum.

c) N-acetylation

O-sulphated K4 polysaccharide deriving from step b) was solubilized in deionized $H_2O$ at room temperature. The solution was added with 0.5 to 2 eq. of NaOH and 0.5 to 2 eq. of acetic anhydride with respect to the moles of O-sulphated K4.

The solution was taken to pH 7.5–8 by sodium hydroxide 2 M and stirred at room temperature for 1–3 hours.

The product was then purified from salts through known techniques as for example through diafiltration using a spiral wrapped membrane by 1000 D.

The process was completed when the conductivity of the permeate was lower than 100 $\mu$S. The obtained product was concentrated till dried under vacuum, at a temperature of 30–60° C.

EXAMPLE 3

Preparation of O-sulphated, N-acetylated K40 Polysaccharide

Firstly the process was carried out through a) N-deacetylation/N-sulphation: 25 g. of purified K40 polysaccharide, is solubilized with 100–1000 ml of sodium hydroxide 2M and maintained at 40–80° C. up to 30 hours, till complete deacetylation.

After the adding of 100–1000 ml of deionized or demineralized water, the solution was taken to a temperature ranging from 20 to 30° C. and to pH 8.00–9.00 by hydrochloric acid.

The solution containing deacetylated K40 was maintained at 20–65° C. and added with 10–60 g of sodium carbonate and 10–60 g of a sulphating agent selected from sulphating reagents as for example the pyridine sulphur trioxide or trimethylamine sulphur trioxide adduct. The adding of sulphating agent was performed in a time up to 6 hours. After completion of the reaction, the solution was taken to a temperature ranging from 20 to 30° C. and to pH 7–7.5 by hydrochloric acid 1M.

The product was purified from salts through known techniques, as for example through diafiltration by using a spiral wrapped membrane by 1000 D.

The process was completed when the conductivity of the permeate was lower than 100 $\mu$S. The obtained product was concentrated under vacuum, cooled down to 4–10° C. and precipitated by ethanol or isopropyl alcohol or acetone.

b) O-sulphation:

N-deacetylated and N-sulphated K40 polysaccharide was solubilized in $H_2O$ and the solution was cooled down to 4–10° C. and then treated on cation-exchange IR-120H$^+$ resin or equivalent.

After the passage of the solution containing the sample, the resin was washed with deionized water.

The solution containing the sample was then neutralized with tertiary or quaternary amine, as for example tetrabutylamonium hydroxide.

The solution was reduced to minimum volume and lyophilized.

The tetrabutylamonium salt was suspended in 20–1000 ml of N,N-DMF or DMSO and added with 15–300 g of a sulphating agent as for example pyridine $SO_3$ adduct in solid form or in solution of N,N-DMF or DMSO. The solution was maintained at 20–70° C., preferably between 40–60° C. for 2–24 hours.

Once the reaction was completed, the solution was cooled down to room temperature and added with acetone saturated with sodium chloride up to complete precipitation.

The precipitate was separated from the solvent by filtration, solubilized with minimum quantity of a 0.2 M NaCl solution and then the solution was taken to pH 7.5–8 with sodium hydroxide 2 M and added with acetone up to complete precipitation.

The obtained precipitate was solubilized with 100–2000 ml of deionized water, purified from residual salts by ultrafiltration as described in step a) and dried under vacuum.

c) N-acetylation

O-sulphated K40 polysaccharide deriving from step b) was solubilized in deionized $H_2O$ at room temperature. The solution was added with 0.5 to 4 eq. of NaOH and 0.5 to 4 eq. of acetic anhydride with respect to the moles of O-sulphated K40.

The solution was taken to pH 7.5–8 by sodium hydroxide 2 M and stirred at room temperature for 1–3 hours.

The product was then purified from salts through known techniques as for example through diafiltration using a spiral wrapped membrane by 1000 D.

The process was completed when the conductivity of the permeate was lower than 100 $\mu$S. The obtained product was concentrated till dried under vacuum, at a temperature of 30–60° C.

EXAMPLE 4

Preparation of O-sulphated Epymerized, N-acetylated K5 Polysaccharide

Firstly the process was carried out through a) N-deacetylation/N-sulphation. This step was identical to step a) in example 1. In the step b) of epimerization, the epimerization in position C5 of glucuronic acid of K5 polysaccharide was performed by the glucuronil C5 epimerase enzyme in solution or in immobilized form The epimerization was carried out through known techniques such as those described in patent WO 01/72848 where C5 epimerase enzyme, natural or recombinant, was immobilized on inert support (a resin functionalized with reactive groups using common techniques of activation and binding for enzymes such as CNBr). 20–1000 ml of solution 25 mM Hepes, 0.1 M KCl, 0.01% triton X100, 0.15 M EDTA at pH 6–7.4, and 0.001–10 g of N-deacetylated N-sulphated K5 polysaccharide are recirculated at 30–160 ml/hr for 1–48 hours in a thermostatic column at 30–40° C., containing $1.2 \times 10^7$ to $3 \times 10^{11}$ cpm eq. of immobilized enzyme. Once the reaction was completed the sample was purified through passage on DEAE resin or by precipitation with 2 volumes of ethanol.

c) O-sulphation

The solution containing the epimerized product derived from previous step was treated according to step b) in example 1.

d) N-acetylation

This step was identical to step c) in example 1.

EXAMPLE 5

Preparation of O-Sulphated Epimerized Partially Desulphated and N-acetylated K5 Polysaccharide a) N-deacetylation/N-sulphation of K5 polysaccharide.

This step was identical to step a) in example 1.

b) Epimerization: this step was identical to step b) in example 4.

c) O-sulphation: this step was identical to step c) in example 4.

d) Partial desulphation.

The solution containing the product resulting from step c) was passed through cation-exchange resin IR-120 $H^+$ or equivalent. The acid solution eluted through $H_2O$ was then neutralized by adding pyridine.

The obtained pyridine salt was added with 20–2000 ml of a solution of DMSO/methanol (9/1 V/V). The solution was maintained at 45–90° C. for 1–8 hours. Once the reaction was completed, the solution was cooled at room temperature added with water and precipitated by acetone saturated with sodium chloride. The obtained solid was solubilized in water and purified through diafiltration on a spiral wrapped membrane having a cut-off of 1000 D and then concentrated and lyophilized under vacuum.

e) N-acetylation

This step was identical to step c) in example 1.

EXAMPLE 6

Preparation of O-sulphated Epimerized, 6O-sulphated and N-acetylated K5 polysaccharide a) N-deacetylation/N-sulphation of K5 or K4 or K40 polysaccharide This step was identical to step a) in example 1.

b) Epimerization

This step was identical to step b) in example 4.

c) O-sulphation

This step was identical to step b) in example 1.

d) Partial desulphation

This step was identical to step d) in example 5.

e) 6O-sulphation

The solution containing the product from step d) was treated as described in step b) in example 1 as to obtain tetrabutylamonium salt.

The solution was then concentrated and lyophilized under vacuum.

Tetrabutylamonium salt was suspended in 20–500 ml of DMF. The suspension was cooled down to 0° C. and treated with a sulphating agent as for example pyridine $SO_3$ adduct.

The solution was kept at 0–5° C. for 0.5–3 hours. Thereafter the solution was treated with acetone saturated with sodium chloride up to complete precipitation.

The obtained precipitate was solubilized with 100–2000 ml of deionized water, purified from residual salts by ultrafiltration and lyophilized under vacuum.

f) N-acetylation

This step was identical to step c) in example 1.

O-sulphated polysaccharides under this invention are characterized by a molecular weight from 1000 to 60.000 Da, by a sulphates/carboxyls ratio ranging from 0.5 to 4.0 and by a N-acetylation percentage ranging from 0 to 99%.

EXAMPLE 7

Inibition of the Production of Pro-inflammatory Cytokines IL1 alpha, IL6 and TNFalpha by the O-sulphated, N-reacetylated K5 Polysaccharide in Mononucleate Human Cells The O-sulphated, N-acetylated K5 polysaccharide produced as described in example 1, has been used for an in vitro test of inhibition of the production of pro-inflammatory cytokines as follows: mononucleate cells deriving from peripheral blood sampled from healthy subjects were used during the trial. Initially, the blood was centrifuged twice at 120 g for 10 minutes to remove platelets; the mononucleate cells were then separated through centrifugation in Ficoll-Hypaque gradient (Boyum A. Scand J. Immunol 5:9, 1976) and washed twice through phosphate buffered saline to remove further contaminants.

The mononucleate cells were re-suspended in buffer RPMI-1640 (GIBCO, Grand Island, N.Y.) containing gentamicin (100 μg/ml).

The mononucleate cells thus obtained from peripheral blood were identified by colouring through α-naphtylacetate esterase and by citometric analysis using OKM14, OKPanB, OKT3 monoclonal antibodies (Ortho Diagnostic System). The percentage of monocytes in the preparation was 20.4%±1.7%, the vital cells (triptan blue method) were 98%, moreover the preparation contained lower than 2% polymorphonucleate leucocytes and lower than 1% platelets.

The levels of cytokines IL-1beta, IL6 and TNF alpha were measured, through an immunoenzymatic method, in the mononucleate cells isolated from peripheral blood, both with or without lipopolysaccharides (lipopolysaccharides from *Escherichia coli* serotype 0111:B4, Sigma USA) as stimulating factor, or in presence of lipopolysaccharides (LPS) and of O-sulphated, N-acetylated K5 polysaccharide (K5OSNAc) prepared as in example 1 at high degree of sulphation (K5OSNAc-H) (sulphates/carboxyl ratio equal or higher than 3) or at low degree of sulphation (K5OSNAc-L) (sulphates/carboxyls ratio lower than 3) after cells incubation at 37° C. in moisturized atmosphere with 5% carbon dioxide for 3 or 4 hours.

The results are in table 1.

O-sulphated, N-sulphated epimerized K5 polysaccharide was also tested and the relevant results are in table 1.

From table 1 it should be noted that the presence of O-sulphated, N-acetylated K5 or O-sulphated N-sulphated epimerized K5 in the suspension of cells after incubation for 3 hours, diminishes the production of cytokines IL-1 beta, IL-6 and TNF-alpha.

Both K5 polysaccharide and the O-sulphated, N-sulphated K5 derivative and the N-sulphated epimerized K5 derivative do not alter or modify in a very small amount, at the same conditions, the production of said cytokines.

The anti-coagulant activity of K5 polysaccharide and K5 polysaccharide derivatives described in table 1 was measured as Xa anti-factor activity in comparison with Xa anti-factor activity of heparin. The Xa anti-factor activity of polysaccharides was between 0 and 15% of the activity found, at the same conditions, for heparin.

TABLE 1

Inhibitory effect of O-sulphated polysaccharides on pro-inflammatory cytokines production after 3 hours incubation (minimum and maximum obtained values).

| Sulphated Polysaccharide | Dilution | Inhibition % of IL1b production in mononucleate cells stimulated by LPS | Inhibition % of IL6 production in mononucleate cells stimulated by LPS | Inhibition % of TNF production in mononucleate cells stimulated by LPS |
|---|---|---|---|---|
| K5 polysacoharide | 1:100 | 0.12–0.84 | 0.01–0.65 | 0.32–0.94 |
| K5 OS,Nac-H (Ex.1) | 1:100 | 36.3–50.95 | 25.58–53.67 | 22.04–62.46 |
| K5 OS,Nac-H (Ex.1) | 1:200 | 16.89–49.17 | 11.61–45.04 | 12.59–43.53 |
| K5 OS,Nac-L (Ex.1) | 1:100 | 18.04–50.48 | 13.92–45.31 | 23.12–50.47 |
| K5 OS, NS (WO 98/09636) | 1:100 | 0.5–4.79 | 9.98–17.8 | 2.19–10.00 |
| K5 OS, NS epi (WO 97/43317) | 1:100 | 39.97–68.37 | 34.07–66.4 | 34.83–73.13 |
| K5 OS, NS epi (WO 97/43317) | 1:200 | 23.29–32.7 | 20.56–37.47 | 20.7–25.31 |
| K5NS epi | 1:100 | nd | nd | 2.2–8.02 |

H: sulphates/carboxyls ratio equal or higher than 3.
L: sulphates/carboxyls ratio lower than 3.
nd: not measured

What is claimed is:

1. Process for the preparation of O-sulphated and N-reacetylated polysaccharides selected from the group consisting of defructosilated K4, K5 and K40, which comprises the following steps:

a) N-deacetylation and N-sulfation of defructosilated K4, K5 and K40 polysaccharides;
   b) O-sulfation; and
   c) N-reacetylation, wherein the O-sulfation is carried out in a homogeneous phase.

2. Process according to claim 1 further comprising a step of epimerization of the N-deacetylated and N-sulfated K5 polysaccharide, carried out before step b).

3. Process according to claim 1 further comprising a step of partial desulfation and a step of 6O-sulfation carried out after step b).

4. Process according to claim 2 further comprising a step of partial desulfation and a step of 6O-sulfation carried out after step b).

5. Process according to claim 1 wherein the N-reacetylation in step c) is essentially carried out by treating a O-sulphated polysaccharide with a solution of acetic anhydride having a concentration from 3% to 20%, at a pH from 7 to 9, at a temperature from 10° C. to 35° C., for a period of at least 1 hour.

6. Process according to claim 5 wherein said N-reacetylation is carried out by addition of 0.5 to 4 equivalents of NaOH and 0.5 to 4 equivalents of acetic anhydride with respect to the moles of O-sulphated polysaccharide, at a pH from 7.5 to 8, and wherein the solution is stirred for a period of from 1 to 3 hours, at a temperature from 20° C. to 30° C.

7. Process according to claim 1 wherein said polysaccharide is the K5 polysaccharide.

8. The process according to claim 1 further comprising at least one purification step selected from the group consisting of polysaccharide precipitation by organic solvents optionally saturated with monovalent salts, diafiltration, and exsiccation.

* * * * *